United States Patent
Raidt et al.

(10) Patent No.: US 9,802,032 B2
(45) Date of Patent: Oct. 31, 2017

(54) CONNECTING MODULE AND SYRINGE HAVING SUCH A CONNECTING MODULE

(71) Applicant: Henke-Sass, Wolf GmbH, Tuttlingen (DE)

(72) Inventors: Simon Raidt, Wurmlingen (DE); Frank Altermann, Tuttlingen (DE)

(73) Assignee: Henke-Sass, Wolf GmbH, Tuttlingen (DE)

( * ) Notice: Subject to any disclaimer, the term of this patent is extended or adjusted under 35 U.S.C. 154(b) by 327 days.

(21) Appl. No.: 14/606,493

(22) Filed: Jan. 27, 2015

(65) Prior Publication Data

US 2015/0209571 A1    Jul. 30, 2015

(30) Foreign Application Priority Data

Jan. 27, 2014  (DE) .................. 10 2014 201 392

(51) Int. Cl.
    *A61M 5/34*     (2006.01)
    *A61M 39/10*    (2006.01)
    (Continued)

(52) U.S. Cl.
    CPC .... *A61M 39/1011* (2013.01); *A61M 5/14216* (2013.01); *A61M 5/204* (2013.01); *A61M 5/31* (2013.01); *A61M 5/3156* (2013.01); *A61M 5/31536* (2013.01); *A61M 5/31563* (2013.01); *A61M 5/3205* (2013.01);
    (Continued)

(58) Field of Classification Search
    CPC .............. A61M 39/10; A61M 39/1011; A61M 2039/1016; A61M 2039/1027; A61M 2039/1033; A61M 2039/1038; A61M 5/344; A61M 5/347; A61M 2005/3206;
    (Continued)

(56) References Cited

U.S. PATENT DOCUMENTS 5,674,206 A * 10/1997 Allton .................. A61M 39/26
                                                    251/149.1
2007/0265577 A1   11/2007  Uematsu et al.
2008/0255542 A1   10/2008  Nimgaard et al.

FOREIGN PATENT DOCUMENTS

EP       1693079 A1    8/2006
JP       H07148271 A   6/1995
(Continued)

*Primary Examiner* — Imani Hayman
*Assistant Examiner* — James D Ponton
(74) *Attorney, Agent, or Firm* — Skaar Ulbrich Macari, P.A.

(57) ABSTRACT

A connecting module is provided with a first connecting component, which has a first fluid channel and a first contact surface, a second connecting component, which has a second fluid channel and a second contact surface. One of the two contact surfaces is formed as an inner surface and the other of the two contact surfaces is formed as an outer surface which is complementary to the inner surface. The connecting module further includes a receiving sleeve with a first threaded section and a first connecting device for the first connecting component. The first connecting component has a second connecting device, which interacts with the first connecting device in such a way that the first connecting component is detachably connected to the receiving sleeve. The second connecting component has a second threaded section which is complementary to the first threaded section.

7 Claims, 4 Drawing Sheets

(51) Int. Cl.
    *A61M 5/31*         (2006.01)
    *A61M 5/32*         (2006.01)
    *A61M 5/142*       (2006.01)
    *A61M 5/20*         (2006.01)
    *A61M 5/315*       (2006.01)

(52) U.S. Cl.
    CPC .......... *A61M 5/3276* (2013.01); *A61M 5/344* (2013.01); *A61M 39/10* (2013.01); *A61M 5/2053* (2013.01); *A61M 5/31551* (2013.01); *A61M 5/31555* (2013.01); *A61M 5/347* (2013.01); *A61M 2005/31508* (2013.01); *A61M 2005/3206* (2013.01); *A61M 2039/1016* (2013.01); *A61M 2039/1033* (2013.01)

(58) Field of Classification Search
    CPC ...... A61M 5/3293; A61M 5/34; A61M 5/345; A61M 2005/3523; A61M 2005/3253
    See application file for complete search history.

(56) References Cited

FOREIGN PATENT DOCUMENTS

| | | | |
|---|---|---|---|
| WO | 02066100 A2 | 8/2002 | |
| WO | 2010028040 A1 | 3/2010 | |
| WO | 2011029056 A2 | 3/2011 | |
| WO | WO2011/159136 A2 * | 12/2011 | ............. A61M 5/34 |

\* cited by examiner

CONNECTING MODULE AND SYRINGE HAVING SUCH A CONNECTING MODULE

PRIORITY

This application claims priority to German Patent Application No. 102014201392.5, filed on Jan. 27, 2014, which is hereby incorporated herein by reference in its entirety.

FIELD

The present invention relates to a connecting module with a first connecting component, which has a first fluid channel and a first contact surface, and a second connecting component, which has a second fluid channel and a second contact surface. Such connecting modules can be formed e.g. as a Luer lock connection and are used, for example, for medical applications, wherein the first connecting component can be a cannula or a tube and the second connecting component can be, for example, part of a syringe. The present invention further relates to a syringe with such a connecting module.

BACKGROUND

When using conventional connecting modules a difficulty often exists that it is difficult to release the connection. If the first connecting component is formed as a cannula, there is always a risk of injury. In particular, the cannula can be contaminated, which leads to a risk of infection.

SUMMARY

An object of the invention includes a connecting module described at the beginning in such a way that it is possible to release the connection safely. The object can be achieved by providing a connecting module, which comprises a first connecting component, which has a first fluid channel and a first contact surface, and a second connecting component, which has a second fluid channel and a second contact surface, wherein one of the two contact surfaces is formed as an inner surface and the other of the two contact surfaces is formed as an outer surface which is complementary to the inner surface, wherein the connecting module further comprises a receiving sleeve with a first threaded section and a first connecting device for the first connecting component, the first connecting component has a second connecting device, which interacts with the first connecting device in such a way that the first connecting component is detachably connected to the receiving sleeve, wherein the second connecting component has a second threaded section which is complementary to the first threaded section and, by screwing the two threaded sections, the two fluid channels are connected to each other and the first contact surface of the first connecting component is brought into contact in a sealing manner with the second contact surface of the second connecting component, and wherein on unscrewing the two threaded sections, the receiving sleeve exerts a force via the two connecting devices to the first connecting component which moves the first contact surface away from the second contact surface.

With the connecting module according to certain embodiments of the invention it is therefore possible easily to release the connection. It is only necessary to unscrew the connection and this can be carried out by actuating the receiving sleeve with the result that the first connecting component, which can be e.g. a cannula, does not have to be handled.

One of the two connecting devices can have a retaining groove and the other of the two connecting devices can have a projection which, in the screwed-in state, projects into the retaining groove.

The receiving sleeve can have a through hole with an inner wall, wherein the first connecting device has the retaining groove which is formed in the inner wall.

The second connecting device can have two, three, four or more projections spaced apart from each another, which project in each case in a direction radial to the first filling channel.

The receiving sleeve can further have a recess at its first end facing away from the connecting component for each projection, which recess extends from the first end to the retaining groove, with the result that the cannula can be inserted via the recess into the retaining groove.

One of the two contact surfaces can be formed as an inner tapered surface (or as an inner conical surface) and the other of the two contact surfaces can be formed as an outer tapered surface (or as an outer conical surface).

The cannula can have a base section on which the first connecting device is formed. In one example, the connection can be formed as a Luer lock connection.

The receiving sleeve can be formed as a receiving nut in which the first threaded section is an internal threaded section.

Furthermore, a syringe is disclosed. The syringe includes a base body, which has a syringe cylinder with an expelling side end, and a plunger rod, the front end section of which is arranged to be displaceable in the syringe cylinder along a displacement direction, in which a connecting module according to the invention is provided, wherein the second connecting component is part of the base body or is connected to this and the second fluid channel is in fluid connection with the syringe cylinder.

In certain embodiments of the syringe, the base body can include a front stop for the plunger rod in the case of which the distance between the front end section and the expelling side end of the syringe cylinder is minimal. In addition, the syringe can comprise a setting element which has a rear stop for the plunger rod in the case of which the distance between the front end section and the expelling side end of the syringe cylinder is maximal, wherein the setting element is movable relative to the base body and can be detachably connected to the base body in at least two predetermined setting positions in which the position of the rear stop is different in the displacement direction, with the result that, by choosing one of the setting positions for the setting element, the maximum travel of the plunger rod can be set.

With the syringe according to certain embodiment of the invention, the maximum travel of the plunger rod and thus the amount to be expelled can therefore be set easily. The set amount to be expelled can thus be repeatedly administered safely.

The syringe can be formed as a self-refilling syringe. By a self-refilling syringe is, in particular, meant a syringe in which the fluid (e.g. medicament) to be administered is filled into the syringe cylinder in the case of a movement of the plunger rod from the front stop to the rear stop and is expelled from the syringe cylinder via the expelling side end in the case of the opposite movement from the rear stop to the front stop.

The setting element can be movable relative to the base body along the displacement direction. For example, the setting element can be formed as a hollow cylinder with a base, wherein the base forms the rear stop.

The base can have a through hole for the plunger rod. The plunger rod can have a lateral projection (e.g. annular) which rests on an inner side of the base when the plunger rod is at the rear stop. The contact between the projection and the inner side of the base thus forms the rear stop.

The plunger rod can be made in one piece or also several pieces. The region of the plunger rod which moves to and fro in the syringe cylinder can also be referred to as a plunger or plunger section.

The setting element can have a spring-loaded pressure piece and the base body can have, in each predetermined setting position, a catch recess for the spring-loaded pressure piece. For example, the base body can have a guide groove or a guide slot for the spring-loaded pressure piece, wherein the guide groove or slot extends along the displacement direction and guides the spring-loaded pressure piece along the displacement direction when the setting element is displaced relative to the base body.

In the syringe according to certain embodiment of the invention, an adjusting groove (or adjusting slot) can, for each predetermined setting position, branch off from the guide groove transverse with respect to the guide groove into which adjusting groove the spring-loaded pressure piece can be brought by means of a relative rotation of the setting element and base body. In particular, each adjusting groove has a catch recess with the result that the desired arrest is produced in interaction with the spring-loaded pressure piece. This arrest can be released by rotation in the opposite direction if the force used is so large that the spring-loaded pressure piece is released from the catch recess.

In the place of a spring-loaded pressure piece, other fixing elements are also possible. For example, jamming can be carried out by a screw which is guided into the setting element and presses against the base body.

In the syringe according to certain embodiment of the invention, the position of the front stop can be fixed. This is very advantageous in particular when formed as a self-refilling syringe since it is possible to fill the syringe cylinder via the expelling side end and all of the fluid can always be expelled from the syringe cylinder.

The syringe can also be described as an injection device and/or an injection system. Further elements which are necessary for the operation of such an injection system are known to a person skilled in the art and can be provided. In particular, the plunger rod can be driven e.g. pneumatically by a compressed air cylinder. For this, the end of the plunger rod facing away from the syringe cylinder can be mechanically connected to the compressed air cylinder.

The syringe can include a cannula which is in fluid connection with the expelling side end of the syringe cylinder such that the fluid can be administered from the syringe cylinder via the cannula. The cannula can be fixed on the base body detachably. For example, the detachable connection can be formed in such a way that the cannula does not have to be handled to be detached.

The cannula can have a first fluid channel and a first contact surface. Furthermore, the base body of the syringe can have a connecting component with a second fluid channel and a second contact surface. The connecting component can be formed by a section of the base body itself or as a separate component connected to the base body.

It is understood that the features mentioned above and those yet to be explained below can be used not only in the stated combinations, but also in other combinations or alone, without departing from the scope of the present invention.

BRIEF DESCRIPTION OF THE DRAWINGS

The invention is explained in further detail below by way of example with reference to the attached drawings which also disclose features essential to the invention.

DETAILED DESCRIPTION

Figure 1:
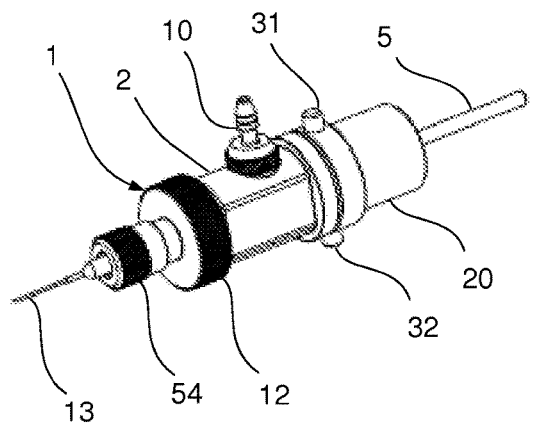
FIG. 1 is a perspective view of a first embodiment of the syringe according to certain embodiments.

The present invention can be explained with reference to the following example embodiments. However, these example embodiments are not intended to limit the present invention to any specific examples, embodiments, environments, applications or implementations described in these embodiments. Therefore, description of these embodiments is only for purpose of illustration rather than to limit the present invention.

In the embodiment shown in FIGS. 1-5, the syringe 1 according to the invention comprises a base body 2 in which a syringe cylinder 3 with an expelling side end 4 (FIGS. 4 and 5) is formed. The syringe 1 comprises a plunger rod 5, the front end section 6 of which is arranged to be displaceable in the syringe cylinder 3 along a displacement direction P1 (in FIGS. 5 and 6 from left to right).

The expelling side end 4 of the syringe cylinder 3 opens out into the base body 2 in a T-shaped channel section 7, in the ends of which are not connected to the expelling side end 4 are arranged a first and second non-return valve 8, 9. The first non-return valve 8 is formed in such a way that, in the case of the plunger rod 5 being drawn back (i.e. a movement from left to right in FIGS. 4 and 5) a fluid, such as e.g. a medicament to be administered, flows or is sucked via a fluid connection 10 and the first non-return valve 8 into the syringe cylinder 3. The fluid can in particular be a liquid. The second non-return valve 9 is formed in such a way that, in the case of an opposite movement of the plunger rod 5 (i.e. from right to left in FIGS. 4 and 5), the fluid located in the syringe cylinder 3 is expelled via the second non-return valve 9 into a channel 11 of an adapter 12 and from the latter through a cannula 13 connected to the adapter 12.

The adapter 12 and the cannula 13 together with a receiving nut form a connecting module, which is described in more detail below in conjunction with FIGS. 7-12. First of all, however, other elements of the syringe 1 are first described.

The syringe 1 is formed in such a way that the maximum travel of the plunger rod 5 and thus the amount of fluid to be dispensed can be set. For this, the base body 2 has a front stop 15 for the plunger rod 5, which front stop is formed by shoulders 16 at the expelling side end 4 of the syringe cylinder 3. The shoulders 16 are formed in that the diameter of the syringe cylinder 3 is larger than the diameter of the adjacent part of the channel of the T-shaped channel section 7.

The front end section 6 of the plunger rod 5 has, at its front end 17, an annular stop surface 18, which rests on the shoulders 16 when the front end section 6 is pushed completely into the syringe cylinder 3. In the embodiment described here, the front end 17 also has a cylindrical projection 19 which then projects into the corresponding part of the T-shaped channel section 7. In an alternative embodiment (not shown), the projection 19 is not provided, with the result that the front end 17 can be formed e.g. planar and has the annular stop surface 18 in its outer region. Furthermore, in the area of the front end section 6, the plunger rod 5 has a sealing ring 14 which sits in a corresponding annular groove. When the annular stop surface 18 rests on the shoulders 16, the distance between the front end 17 and the expelling side end 4 is minimal.

The syringe 1 further has a sleeve-shaped setting element 20 which defines a rear stop 21 for the plunger rod 5 in the case of which the distance between the front end 17 and the expelling side end 4 of the syringe cylinder 3 is maximal. For this, a through hole 23, through which the plunger rod 5 runs, is formed in the base 22 of the setting element 20 which has a U-shaped cross-section. In the embodiment described here, inserted in the through hole 23 is a guide sleeve 24, which defines an opening in the base 22 which is coaxial with the syringe cylinder 3 and has a smaller diameter than the syringe cylinder 3.

The plunger rod 5 is formed in such a way that the front end section 6 has an external diameter which is adapted to the syringe cylinder 3 and thus serves as a plunger. A rear section 25 of the plunger rod 5, which has a smaller diameter than the front end section 6, is attached to the front end section 6. The diameter of the rear section 25 is adapted to the opening defined by the guide sleeve 24. Furthermore, the front end section 6 has, on its end facing away from the front end 17 to which the rear section 25 of the plunger rod 3 is attached, a substantially annular projection 26 which, in the cross-sectional representations according to FIGS. 4 and 5 rests on an inner side 27 of the base 22. The inner side 27 thus forms the rear stop 21 for the plunger rod 5 since it is not possible to pull the plunger rod 5 out of the syringe cylinder 3 beyond this position.

The setting element 20 is, as is described below in detail, displaceable relative to the base body 2 in the displacement direction P1 of the plunger rod 5 and can be fixed or arrested at predetermined setting positions to the base body 2 with the result that, by this means, the position of the rear stop 21 can be set and altered in the displacement direction P1. In the syringe 1 according to the invention, the front stop 15 is fixed, or its position cannot be altered, while the rear stop 21 can be adjusted. By setting the position of the rear stop 21 in this way, the maximum travel of the plunger rod 5 and thus the maximum amount of fluid which can be expelled with a single movement of the plunger rod (displacing the plunger rod 5 from its rear stop position to its front stop position) are determined.

Figure 3:
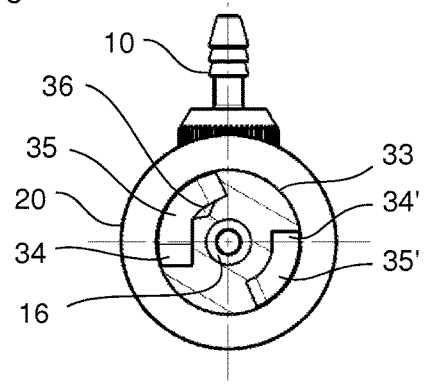
FIG. 3 is a sectional representation according to the section line A-A in FIG. 2.
Figure 4:
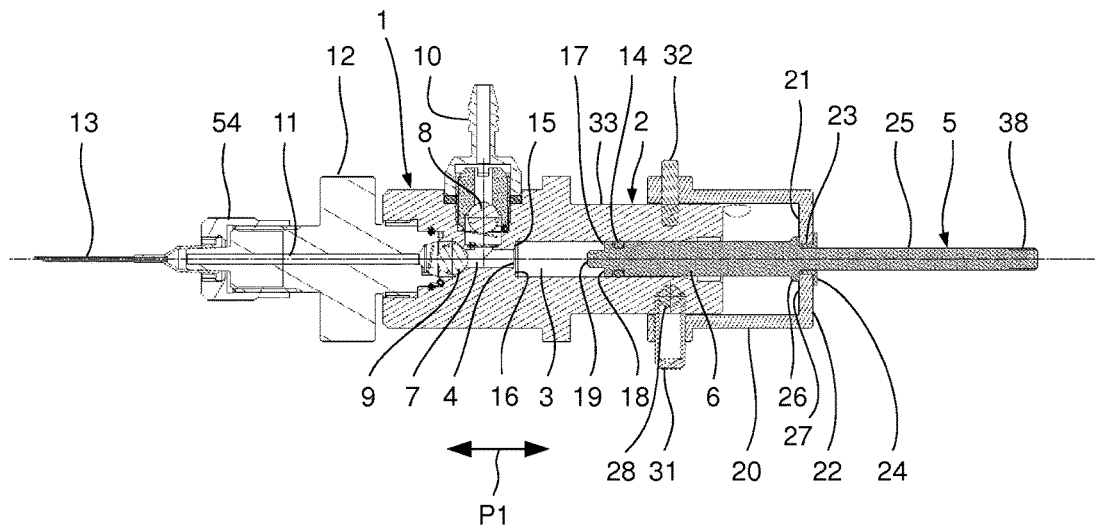
FIG. 4 is a longitudinal sectional representation of the syringe according to certain embodiments in which the rear stop is in a first predetermined setting position.
Figure 5:
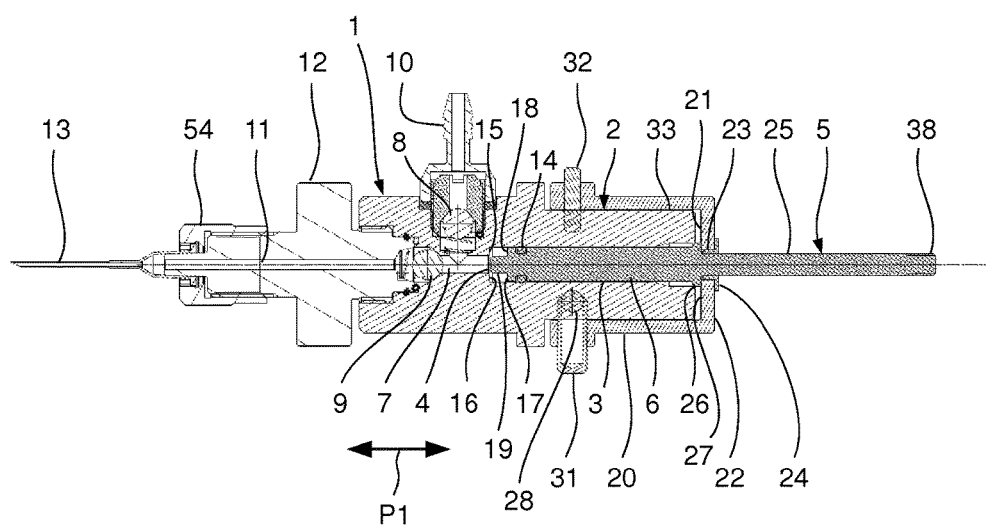
FIG. 5 is a sectional representation according to FIG. 4 in which the rear stop is in a second predetermined setting position.

As can be seen in FIGS. 4 and 5, the setting element 20 has, in the region of its front open end 30, a spring-loaded pressure piece 31 and a pin 32, which extend in each case in the radial direction and are arranged opposite each other. The spring-loaded pressure piece 31 has, on its end projecting inwards, a ball 28 which is loaded by means of a spring, which is not shown, with a force in the direction to the syringe cylinder 3 and serves to arrest the setting element 20. The pin 32 and the spring-loaded pressure piece 31 are arranged in the front open end 30 in such a way that they project inwards beyond an inner wall of the setting element 20. The diameter of the inner wall of the setting element 20 corresponds to the external diameter of the base body 2 in its rear end section 33 in which the syringe cylinder 3 is formed. In order to make it possible to displace the setting element 20 relative to the base body 2 or on the rear end section 33 of the base body 2, both for the spring-loaded pressure piece 31 and also for the pin 32, a guide groove 34, 34' extending in the displacement direction is formed on the outer side of the rear end section 33. The guide groove 34 for the spring-loaded pressure piece 31 can be seen in the perspective exploded representation according to FIG. 2. Both guide grooves 34, 34' are visible in the sectional representation in FIG. 3 (cut along A-A in FIG. 2). Four adjusting grooves 35, 35' go off in each case from the guide groove 34 as well as from the guide groove 34', which adjusting grooves extend in each case in the circumferential direction of the rear end section 33 along a predetermined angle range. The adjusting grooves 35 for the spring-loaded pressure piece 31 each end in a catch recess 36. In the embodiment example described here, two of the four adjusting grooves 35 extend clockwise and the other two adjusting grooves 35 extend anticlockwise. The same applies to the adjusting grooves 35'. In the displacement direction (double arrow P1 in FIGS. 2, 4 and 5), the four adjusting grooves 35 and the four adjusting grooves 35' are each spaced apart from each other such that four predetermined setting positions are available. However, the guide groove 34' for the pin 32 and the corresponding adjusting grooves 35', which are not visible in FIG. 2, have a smaller width due to the smaller diameter of the pin 32 compared with the spring-loaded pressure piece 31. Furthermore, the adjusting grooves 35' for the pin 32 do not end in a catch recess.

In the sectional view according to FIG. 3 an adjusting groove 35 is shown which ends with a catch recess 36. The corresponding adjusting groove 35' for the pin 32 ends without a catch recess.

Figure 2:
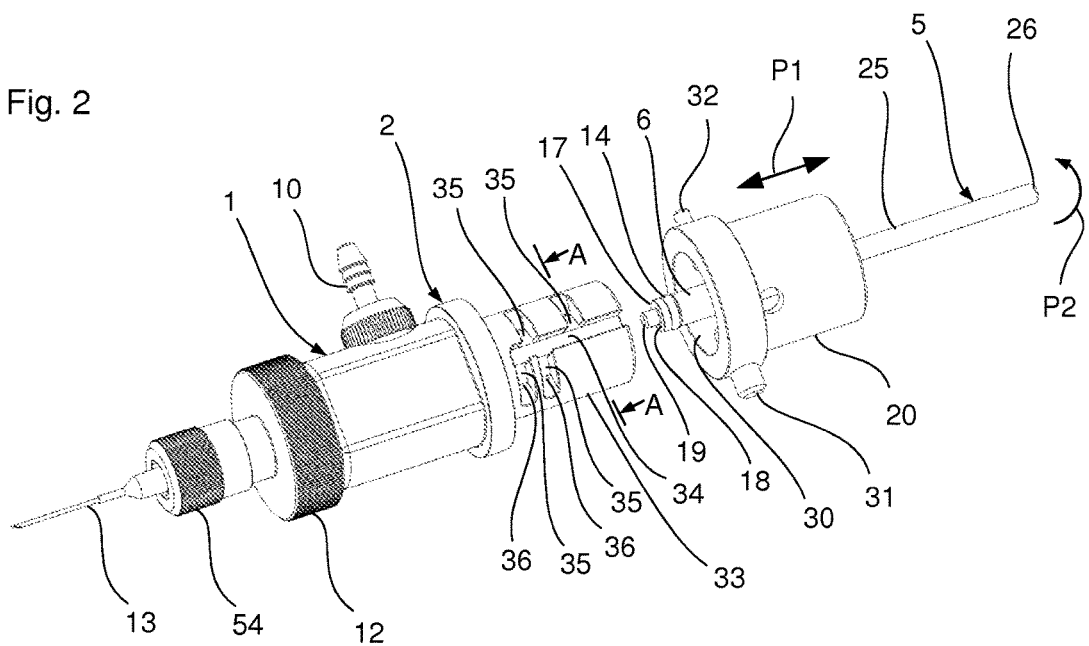
FIG. 2 is a perspective exploded representation of the syringe of FIG. 1.

In order to set a desired maximum travel of the plunger rod, starting from the exploded representation in FIG. 2 the setting element 20 is to be turned anticlockwise (direction of rotation according to arrow P2 in FIG. 2) by 90°, with the result that the end (with the ball 28) of the spring-loaded pressure piece 31 projecting inwards can be moved along the guide groove 34. The setting element 20 is then to be moved along the displacement direction P1 such that the spring-loaded pressure piece 31 is at the level of the desired adjusting groove 35 and the setting element 20 is then arrested by rotating it in the direction of the catch recess 36 of the chosen adjusting groove 35 (i.e. either clockwise or anticlockwise), since on reaching the catch recess 36, the ball 28 of the spring-loaded pressure piece 31 is pressed into the catch recess 36.

The maximum travel of the plunger rod according to the invention can thus be set. The syringe 1 therefore has different catch positions for the rear stop 21.

In the embodiment described here, the plunger rod 5 is driven pneumatically by a compressed air cylinder which is not shown. The corresponding connection can be made with the end 38, facing away from the base body 2, of the rear section 25 of the plunger rod 5. In the embodiment described, an external thread is formed at the end 38 of the plunger rod 5.

Figure 6:
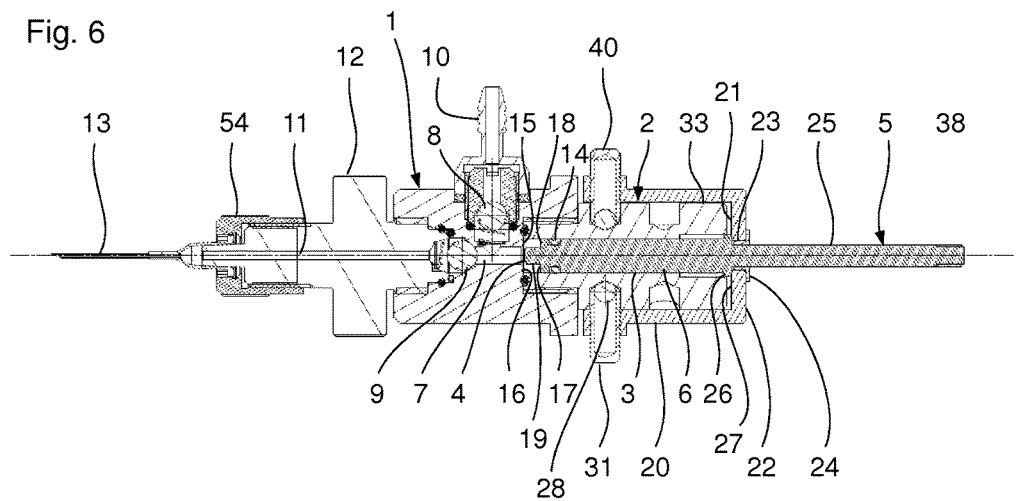
FIG. 6 is a sectional representation according to FIG. 5 of a modification of the syringe according to certain embodiments.
Figure 7:
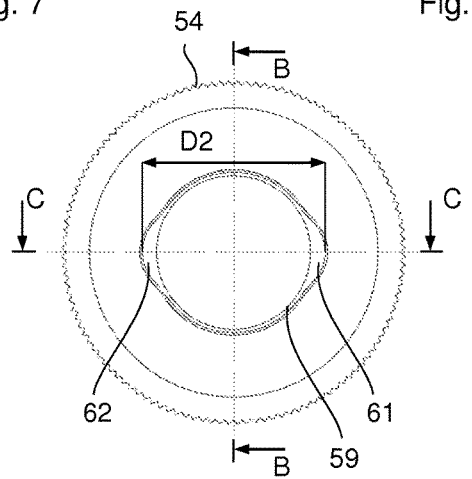
FIG. 7 is a top view of the nut of the syringe according to certain embodiments.
Figure 8:
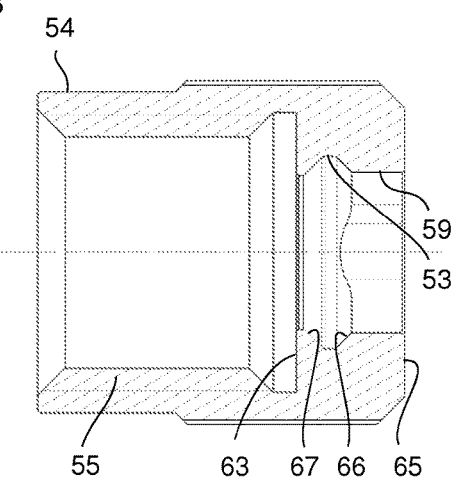
FIG. 8 is a sectional view of the receiving nut along the section line B-B in FIG. 7.
Figure 9:
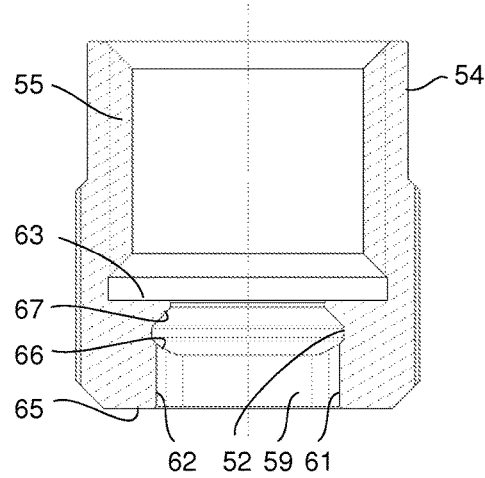
FIG. 9 is a sectional view of the receiving nut along the section line C-C in FIG. 7.

In FIG. 6 a sectional view according to FIGS. 4 and 5 is shown in a modification of the syringe 1 according to the invention. The syringe 1 according to FIG. 6 differs from the syringe 1 described hitherto in that instead of the pin 32 a second spring-loaded pressure piece 40 is provided. The corresponding guide groove 34' and the corresponding adjusting grooves 35' are therefore formed in the same way as for the spring-loaded pressure piece 31 of the embodiment described hitherto. In particular, the adjusting grooves 35' for the second spring-loaded pressure piece 40 each have a catch recess. The rest of the design of the syringe 1 according to FIG. 6 corresponds to the design of the syringe of FIGS. 1 to 5 such that identical elements are given identical reference symbols and for the description thereof reference is made to the above statements.

In the embodiments according to FIGS. 1 to 6, the cannula 13 is detachably attached to the adapter 12, wherein the adapter 12 is detachably connected (via a screw connection) to the base body 2. The connection between cannula 13 and adapter 12 is described below in conjunction with FIGS. 7-12 and is formed as a so-called Luer lock connection, wherein the adapter 12 has, on its end facing away from the syringe cylinder 3, an outer tapered section 50 on which sits a corresponding inner tapered section 51 of a base 52 of the cannula 13. An annular projection 49 of the base 52 of the cannula 13 sits in an annular retaining groove 53 of a receiving nut 54 which is screwed onto the adapter 12. For this, the receiving nut 54 has an internal threaded section 55 and a corresponding external threaded section 56 is formed on the adapter 12.

Figure 10:
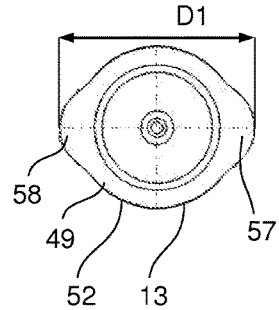
FIG. 10 is a top view of the cannula according to certain embodiments.
Figure 11:
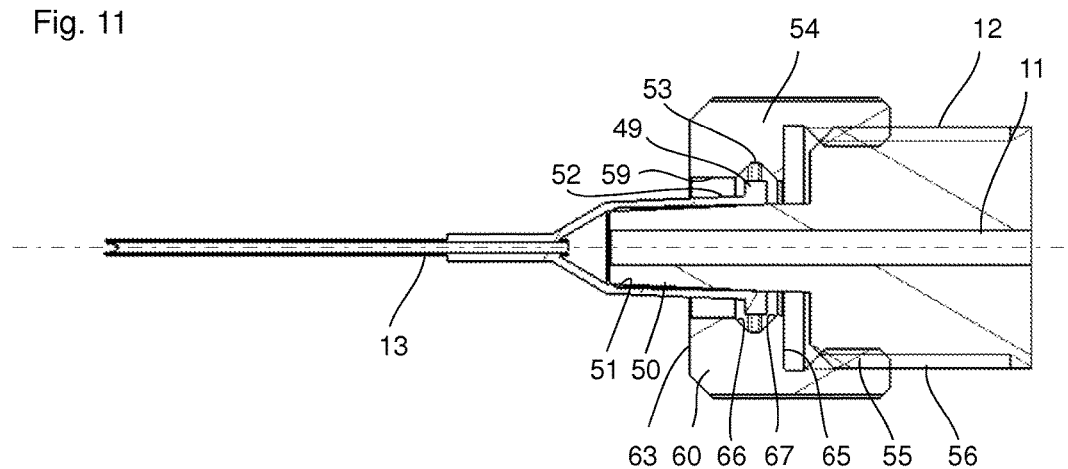
FIG. 11 is an enlarged sectional representation of the cannula, the receiving nut and the adapter of the syringe according to certain embodiments.

As can be seen in particular from the top view of the cannula 13 in FIG. 10, the outline of the annular projection 49 of the foot 52 is substantially circular and has two opposite lateral projections 57, 58, with the result that thereby a deviation from the circular shape is present.

The retaining groove 53 is formed on an inner side of a through hole 59 in the base 60 of the receiving nut 54 of substantially U-shaped cross-section (FIGS. 8, 9, 11, 12). The region of the through hole 59, which runs from the front end 65 of the receiving nut 54 facing away from the adapter 12 to the retaining groove 53, has, in cross-section, an outline which corresponds to the outline of the annular projection 49 of the cannula 13. As can be seen in particular in the top view of FIG. 7, the outline of the through hole 59 is substantially circular and has two recesses 61, 62 projecting radially outwards. However, these recesses 61 and 62 of the through hole 59 only extend from the front end 65 to the retaining groove 53. In the region from the retaining groove 53 to the inner side 63 of the base 60 facing the adapter 12 the recesses 61 and 62 are not formed with the result that here the through hole 59 only has a circular cross-sectional shape.

Figure 12:
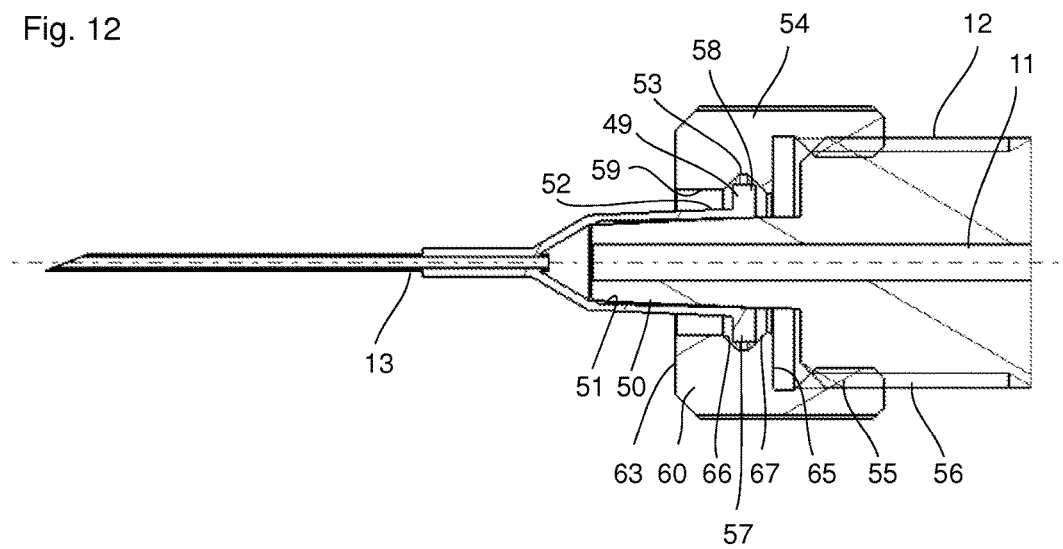
FIG. 12 is a sectional view according to FIG. 11, wherein the cannula is rotated about its longitudinal axis by 90° vis-à-vis the position according to FIG. 11.

The through hole 59 with the recesses 61 and 62 is formed such that the annular projection 49 of the cannula 13 can be inserted from the front end 65 of the receiving nut 54 up to the retaining groove 53. Once the annular projection 49 is inserted into the retaining groove 53 in this way (FIG. 11), the cannula 13 can be rotated relative to the receiving nut 54 about the longitudinal axis of the cannula 13, whereby the projections 57 and 58 are positioned in a region in the retaining groove 53 in which no recesses 61 and 62 are formed, with the result that the cannula 13 sits in the retaining groove 53 (FIG. 12).

The maximum extension D1 of the annular projection, which is determined by the two projections 57 and 58, is preferably chosen such that it is slightly larger than the maximum inner width D2 of the through hole 59 available by means of the recesses 61, 62. In this case, for insertion in the receiving nut 54, the cannula 13 must be slightly tilted (vis-à-vis the plane of drawing of FIG. 7). It is thus possible, despite the larger extension D1 of the projections 57 and 58, to insert the annular projection 49 of the cannula 13 into the receiving nut 54 through the recesses 61, 62 up to the retaining groove 53. The thickness of the retaining groove 53 (extension from left to right in FIG. 8) is chosen such that the base 52 and thus also the annular projection 49 of the cannula 13 can be tilted back in the retaining groove 53 again (there is thus sufficient play between the annular projection 49 and the retaining groove 53), with the result that, even without rotating the cannula 13 relative to the receiving nut 54, a certain retaining function is already provided by the retaining groove 53.

When the receiving nut 54 is screwed on with cannula 13 inserted, the projections 57 and 58 rest on the front side 66 of the retaining groove 53, with the result that by this means the inner tapered section 51 (or inner cone section 51) of the cannula 13 is pressed onto the outer tapered section 50 (or outer cone section) of the adapter 12. By means of the flat contact of the two tapered sections 50, 51 a seal effect is achieved. The desired fluid seal between the channel 11 and the cannula 13 is thus realised and a use of the syringe 1 as intended is possible.

When the cannula 13 is to be exchanged, only the receiving nut 54 needs to be unscrewed. During this unscrewing, the rear side 67 of the retaining groove 53 then presses against the projections 57, 58 of the base or foot 52 of the cannula 13 and thus pulls the cannula 13 off the inner tapered section 50 of the adapter 12 automatically. It is thus possible to safely detach the cannula 13 since the cannula 13 itself does not need to be handled. Solely by unscrewing of the receiving nut 54, the cannula 13 is detached from the adapter 12.

The connecting module (cannula 13, adapter 12 and receiving nut 54) was described here in conjunction with the syringe 1 only by way of example. In the connecting module according to the invention, instead of a cannula 13, another element with a fluid channel, which has a base 52 in the manner described, can also be used. For example, a tube can be connected in this way. Also, the adapter 12 does not have to be a separate element but can be part of the base body 2 or can also be replaced by another element with a fluid channel 11. The essential factor here is that there is a detachable connection between the two connecting components 13, 12 to be connected, in the case of which the connection is detached simply by unscrewing the receiving nut 54.

The above disclosure is related to the detailed technical contents and inventive features thereof. People skilled in this field may proceed with a variety of modifications and replacements based on the disclosures and suggestions of the invention as described without departing from the characteristics thereof. Nevertheless, although such modifications and replacements are not fully disclosed in the above descriptions, they have substantially been covered in the following claims as appended.

The invention claimed is:

1. A connecting module, comprising:
a first connecting component, which includes a first fluid channel and a first contact surface;
a second connecting component, which includes a second fluid channel and a second contact surface, wherein one of the first and second contact surfaces is formed as an inner surface and the other of the first and second contact surfaces is formed as an outer surface which is complementary to the inner surface;
a receiving sleeve including a first threaded section and a first connecting device;
wherein the first connecting component includes a second connecting device, the second connecting device interacting with the first connecting device such that the first connecting component is detachably connected to the receiving sleeve,
wherein the second connecting component includes a second threaded section which is complementary to the first threaded section and by screwing the two threaded sections, the two fluid channels are connected to each other and the first contact surface of the first connecting component is brought into contact in a sealing manner with the second contact surface of the second connecting component in a screwed-in state,
wherein upon unscrewing the two threaded sections, the receiving sleeve exerts a force via the two connecting devices to the first connecting component which moves the first contact surface away from the second contact surface,
wherein the receiving sleeve includes a through hole with an inner wall,
wherein the first connecting device defines a retaining groove which is formed in the inner wall, and
wherein the second connecting device defines a first projection and a second projection, each spaced apart from each other, the first and second projections projecting in each case in a direction radial to the first fluid channel and, in the screwed-in state, into the retaining groove.

2. The connecting module according to claim 1, wherein the receiving sleeve, at a first end located nearest the first connecting component, includes, for each of the first projection and the second projection, a recess which extends from the first end to the retaining groove, such that the first connecting component can be inserted via the recesses into the retaining groove.

3. The connecting module according to claim 1, wherein one of the first and second contact surfaces is formed as an inner tapered surface and the other of the first and second contact surfaces is formed as an outer tapered surface.

4. The connecting module according to claim 1, wherein the first connecting component comprises a cannula with a base and the second connecting device is formed on the base.

5. The connecting module according to claim 1, wherein the connecting module is formed as a Luer lock connection.

6. The connecting module according to claim 1, wherein the receiving sleeve is formed as a receiving nut in which the first threaded section is formed as an internal threaded section.

7. A syringe, comprising:
a base body, including a syringe cylinder having an expelling side end;
a plunger rod, including a front end section displaceable within the syringe cylinder along a displacement direction; and
a connecting module, comprising:
a first connecting component, which includes a first fluid channel and a first contact surface;
a second connecting component, which includes a second fluid channel and a second contact surface, wherein one of the first and second contact surfaces is formed as an inner surface and the other of the first and second contact surfaces is formed as an outer surface which is complementary to the inner surface;
a receiving sleeve including a first threaded section and a first connecting device;
wherein the first connecting component includes a second connecting device, the second connecting device interacting with the first connecting device such that the first connecting component is detachably connected to the receiving sleeve,
wherein the second connecting component includes a second threaded section which is complementary to the first threaded section and by screwing the two threaded sections, the two fluid channels are connected to each other and the first contact surface of the first connecting component is brought into contact in a sealing manner with the second contact surface of the second connecting component in a screwed-in state, and
wherein upon unscrewing the two threaded sections, the receiving sleeve exerts a force via the two connecting devices to the first connecting component which moves the first contact surface away from the second contact surface,
wherein the receiving sleeve includes a through hole with an inner wall,
wherein the first connecting device defines a retaining groove which is formed in the inner wall, and
wherein the second connecting device defines a first projection and a second projection, each spaced apart from each other, the first and second projections projecting in each case in a direction radial to the first fluid channel and, in the screwed-in state, into the retaining groove,
wherein the second fluid channel of the second connecting component is in fluid connection with the syringe cylinder.

* * * * *